United States Patent
Meier et al.

(10) Patent No.: US 8,442,782 B2
(45) Date of Patent: May 14, 2013

(54) METHOD FOR DETERMINING AND/OR MONITORING A PROCESS VARIABLE OF A MEDIUM, AND CORRESPONDING APPARATUS

(75) Inventors: Jürgen Meier, Maulburg (DE); Alexander Müller, Sasbach-Jechtingen (DE); Sascha D'Angelico, Rümmingen (DE); Franco Ferraro, Schwörstadt (DE); Walter Rombach, Rheinfelden (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 653 days.

(21) Appl. No.: 12/449,308

(22) PCT Filed: Feb. 13, 2008

(86) PCT No.: PCT/EP2008/051703
§ 371 (c)(1),
(2), (4) Date: Dec. 23, 2009

(87) PCT Pub. No.: WO2008/101843
PCT Pub. Date: Aug. 28, 2008

(65) Prior Publication Data
US 2010/0161251 A1     Jun. 24, 2010

(30) Foreign Application Priority Data
Feb. 20, 2007     (DE) .................... 10 2007 008 669

(51) Int. Cl.
*G01F 17/00*     (2006.01)
*G01F 23/00*     (2006.01)
*G01L 7/00*     (2006.01)
*G01N 11/00*     (2006.01)
*G01R 13/00*     (2006.01)
*G01R 29/26*     (2006.01)

(52) U.S. Cl.
USPC ................... 702/55; 702/50; 702/54; 702/72

(58) Field of Classification Search ................... 702/72, 702/50, 54, 55, 100, 107
See application file for complete search history.

(56) References Cited

U.S. PATENT DOCUMENTS
4,535,637 A * 8/1985 Feller .................... 73/861.77
5,295,084 A * 3/1994 Arunachalam et al. ......... 702/50
(Continued)

FOREIGN PATENT DOCUMENTS
DE     10 2004 055 552 A1     5/2006
DE     10 2005 015 547 A1     10/2006
(Continued)

OTHER PUBLICATIONS
Translation of DE 102006034105 A1, Jan. 24, 2008.*
(Continued)

*Primary Examiner* — Michael Nghiem
*Assistant Examiner* — Yaritz H Perez Bermudez
(74) *Attorney, Agent, or Firm* — Bacon & Thomas, PLLC

(57) ABSTRACT

A method for determining and/or monitoring a process variable of a medium, wherein a mechanically oscillatable unit is supplied with an exciter signal wherein a received signal coming from the mechanically oscillatable unit is received, and wherein the exciter signal is produced in such a manner, that a phase difference between the exciter signal and the received signal equals a predeterminable phase value. A criterion for judging the determining of the phase difference between the exciter signal and the received signal, or a signal dependent on the exciter signal or on the received signal, is established; in the case, in which the criterion for judging the determining of the phase difference is fulfilled, tuning of the phase difference is closed-loop controlled; and, in the alternative case, tuning of the phase difference is open-loop controlled. An apparatus associated with the method is also disclosed.

18 Claims, 3 Drawing Sheets

U.S. PATENT DOCUMENTS

| | | | | |
|---|---|---|---|---|
| 5,339,258 A * | 8/1994 | Stabinger et al. | ............... | 702/50 |
| 6,148,665 A * | 11/2000 | Getman et al. | ............. | 73/290 V |
| 6,236,322 B1 * | 5/2001 | Lopatin et al. | ................ | 340/612 |
| 7,874,199 B2 * | 1/2011 | Chaudoreille et al. | ........ | 73/32 A |
| 2004/0078164 A1 | 4/2004 | Lopatin | | |
| 2005/0052813 A1 | 3/2005 | Kobayashi | | |
| 2006/0131994 A1 * | 6/2006 | D'Angelico et al. | ......... | 310/317 |
| 2009/0205411 A1 * | 8/2009 | Muller | ......................... | 73/64.53 |
| 2010/0083752 A1 * | 4/2010 | Malinek | ....................... | 73/32 R |

FOREIGN PATENT DOCUMENTS

| | | |
|---|---|---|
| DE | 10 2006 034 105 A1 | 1/2008 |
| EP | 1 580 539 A1 | 9/2005 |

OTHER PUBLICATIONS

Translation of DE 102005015547 A1, Oct. 5, 2006.*
Translation of DE 102004055552, May 18, 2006.*
English translation of the Inernational Preliminary Examination Report, Sep. 13, 2009, WIPO, Switzerland.

* cited by examiner

METHOD FOR DETERMINING AND/OR MONITORING A PROCESS VARIABLE OF A MEDIUM, AND CORRESPONDING APPARATUS

TECHNICAL FIELD

The invention relates to a method for determining and/or monitoring at least one process variable of a medium, wherein at least one mechanically oscillatable unit is supplied with an exciter signal, wherein at least one received signal coming from the mechanically oscillatable unit is received, wherein the exciter signal is produced in such a manner, that a phase difference between the exciter signal and the received signal essentially equals a predeterminable phase value. Furthermore, the invention relates to an apparatus for determining and/or monitoring at least one process variable of a medium. The apparatus includes: at least one mechanically oscillatable unit; at least one driving/receiving unit, which excites the mechanically oscillatable unit to execute mechanical oscillations and which receives mechanical oscillations of the mechanically oscillatable unit; and at least one electronics unit, which supplies the driving/receiving unit with an electrical exciter signal and which receives an electrical received signal from the driving/receiving unit. The medium is, for example, a liquid or a bulk good. The process variable is, for example, the fill level, the density or the viscosity of the medium. The medium is located, for example, in a container or in a pipe.

BACKGROUND DISCUSSION

Known in the state of the art are measuring devices, in the case of which a so-called oscillatory fork or a single rod or a membrane, as mechanically oscillatable unit, is excited to execute oscillations. Since the oscillations, or their characterizing variables, such as frequency, amplitude and phase, are dependent on the contact with a medium, or on properties of the medium, such as density or viscosity, conclusions regarding the measured variables can be drawn from the characterizing variables of the oscillations. Therefore, such a measuring device permits, for example, the monitoring of fill level or the measuring of density.

It has been found, that there are regions of phase difference between the exciter and the received signal, in which the behavior of the oscillatory system can be influenced. Thus, the detecting of foam can be enabled or suppressed. Furthermore, the dependence of the oscillations on changes of viscosity can be canceled (see DE 100 57 974 A1). In order to achieve these effects, it is, however, required, that the desired phase values be set as exactly as possible. A problem, however, is that the measuring of the phases is not always optimally possible.

SUMMARY OF THE INVENTION

An object of the invention is to provide a method for determining or monitoring a process variable, wherein the phase difference between the exciter signal and the received signal is always tuned as optimally as possible. Another object is to provide a corresponding apparatus.

The object is achieved, according to the invention, by a method, which provides that: at least one criterion for judging the determining of the phase difference between the exciter signal and the received signal, or a signal dependent on the exciter signal or on the received signal, is established; in the case, in which the criterion for judging the determining of the phase difference is fulfilled, tuning of the phase difference is closed-loop controlled; and in the case, which is alternative to the case, that the criterion for judging the determining of the phase difference is fulfilled, tuning of the phase difference is open-loop controlled.

In the case of closed-loop control, the result (output variable) has, via feedback, an influence on the manipulated variable. I.e., in contrast to open-loop control, feedback takes place. Thus, one speaks of closed control loop. In contrast, open-loop control has no feedback. An open-loop control does not take the output value, or state of the variable to be controlled, into consideration. Due to the interrupted feedback of the actual variable, one speaks, in control theory, of an open control loop.

In the method of the invention, the phase difference between the exciter signal and the received signal is closed-loop controlled in the case wherein the determining of the phase difference between the exciter signal or the received signal, or a signals dependent on the exciter signal or on the received signal, satisfies a predeterminable criterion. The criterion serves, thus, to detect, whether the phase difference can be ascertained sufficiently exactly, that, therewith, a closed-loop control of the tuning of the phase difference is possible. If the criterion is not fulfilled, i.e. the alternative case to the preceding case is present, then the determining of the phase difference is qualitatively not sufficiently exact, in order, therewith, to perform a closed-loop control, whereupon an open-loop control is performed. For this, preferably, stored data are used.

Or, in other words: If the phase difference can be reliably determined, then the tuning of the difference is closed-loop controlled. If the determining of the phase difference is not precise enough, then tuning of the phase difference is open-loop controlled.

An embodiment of the method of the invention provides that tuning of the phase difference is closed-loop controlled, until the phase difference essentially equals the predeterminable phase value. I.e., based on repeated determining of the phase difference, a manipulated variable, for example, for activating a phase shifter in the feedback electronics, is altered, until the phase difference corresponds to the desired phase value.

An embodiment of the method of the invention includes that at least one characteristic variable of the exciter signal and/or the received signal and/or a signal dependent on the exciter signal and/or on the received signal is used for the open-loop control. Thus, at least one characteristic variable of at least one signal is ascertained and, based on the characteristic variable and in combination with known open-loop control variables, then tuning of the phase difference is suitably open-loop controlled. Thus, for example, the frequency of the exciter signal is taken as a measure for the phase difference, in order, then, as a function of the stored data, e.g. to adjust a phase shifter suitably.

An embodiment of the method of the invention provides, that the received signal is preamplified to a preamplified signal, and that the phase difference between the exciter signal and the preamplified signal is ascertained and closed-loop controlled or open-loop controlled. In this embodiment, not the received signal is used for the closed-loop control, or open-loop control, or for determining the phase difference, but, instead, the received signal is first amplified to a preamplified signal, and this preamplified, or also smoothed, signal is then taken into consideration for determining the phase difference.

An embodiment of the method of the invention includes, that the frequency of the exciter signal and/or the received signal and/or the preamplified signal is used for open-loop control of the tuning of the phase difference. For the open-loop control, it is required, that at least one characteristic variable of the signals to be adjusted be known. Corresponding to this characteristic variable and based on the stored data, then the manipulated variables or the manipulated variable are/is suitably altered, so that the desired effect should occur, i.e. that the phase is equal to the predeterminable value. In this case, a frequency of at least one of the involved signals is taken into consideration for the open-loop control.

An embodiment of the method of the invention provides, that data produced and stored in manufacture, and/or updated data, are used for the open-loop control of the tuning of the phase difference. Preferably, a first set of data for the open-loop control of the tuning of the phase difference is produced in the manufacturing and suitably stored in the measuring device. In an additional variant, these data are produced and stored in an installing of the measuring device on-site, i.e. before the first start-up. The updating of the data is preferably performed during operation of the measuring device, i.e., for example, in the installed state, i.e., thus, also with real process data.

An embodiment of the method of the invention includes that in the case, in which the criterion for judging the determining of the phase difference is fulfilled, the data for the closed-loop control are compared with the stored and/or updated data for the open-loop control of the tuning of the phase difference, and that, in the case of a deviation outside of a predetermined limit value, the data for the open-loop control are updated with the newly acquired data and stored. In this embodiment, thus, an adapting of the control data is performed. If the criterion for a reliable phase difference ascertainment is fulfilled, i.e. a closed-loop control is possible, then the manipulated variable values, which result from the closed-loop control, are compared with the data stored for this state for the open-loop control. If a deviation is found between the values, which can happen, for example, as a result of an aging process in the measuring device, then the stored data, or, on occasion, already previously updated data, are updated with the new data acquired from the closed-loop control. I.e., from this control point in time, the updated data are used for subsequent open-loop controlling.

An embodiment of the method of the invention includes, that the newly acquired data and the stored data are exploited for predictive maintenance. From the development of the data for the open-loop control, thus, it is attempted to detect a tendency and, on occasion, to predict developments.

An embodiment of the method of the invention provides that, in predetermined time intervals, the data for the open-loop control of the tuning of the phase difference are produced automatically. Alternatively, this happens on the basis of a control command. For such purpose, suitable values are produced, the behavior is evaluated and the open-loop control data are stored.

An embodiment of the method of the invention includes, that an oscillatory fork or a single rod or a membrane, as mechanically oscillatable unit, is supplied with the exciter signal.

An embodiment of the method of the invention provides, that a tube, in which the medium is, at least at times, located, is supplied, as mechanically oscillatable unit, with the exciter signal.

An embodiment of the method of the invention provides, that at least density or fill level or viscosity or flow of the medium is ascertained and/or monitored.

Furthermore, the invention achieves the object as regards the apparatus by the features that: at least one phase measuring unit is provided in the electronics unit; at least one adjustable phase shifter is provided in the electronics unit; and at least one phase tuning unit is provided in the electronics unit.

An embodiment of the apparatus of the invention provides, that the phase tuning unit is embodied in such a manner, that the phase tuning unit judges the quality of at least one measuring undertaken by the phase measuring unit of a phase of an electrical signal or a phase difference between two signals and that the phase tuning unit, based on the evaluating, either closed-loop controls or open-loop controls, with use of the phase shifter, the tuning of a phase difference between the exciter signal, or a signal dependent on the exciter signal, and the received signal, or a signal dependent on the received signal. For the closed-loop control of the tuning a phase difference, it is required, that at least one phase be measurable sufficiently exactly. Thus, in this embodiment, at least one measuring of at least one phase is qualitatively judged and, based on the evaluating, tuning of the phase difference is performed either by closed-loop control or by open-loop control. Alternatively, the quality of the measuring of the phase difference is taken into consideration for deciding, whether a closed-loop control or an open-loop control takes place.

An embodiment of the apparatus of the invention includes, that the phase tuning unit judges, on the basis of at least one of predeterminable criterion, the quality of at least one measuring undertaken by the phase measuring unit of a phase of an electrical signal or a phase difference between two signals. A criterion for evaluating two phase measurements is, for example, whether the two signals, of which, in each case the phase is to be ascertained, have the same frequency and/or the same curve form and/or the same signal pause ratio. A criterion for judging the measuring of the phase of a signal is whether the phase values obtained, respectively, from the rising edges and from the falling edges are, in each case, equal.

An embodiment of the apparatus of the invention provides, that at least one memory unit is provided, in which data for the open-loop control of the tuning of the phase difference are storable.

An embodiment of the apparatus of the invention includes, that the phase tuning unit is embodied in such a manner, that the phase tuning unit, in the case, in which the measuring of the phase or the phase difference fulfills the predeterminable criterion, closed-loop controls the tuning of the phase difference using the phase shifter, and that the phase tuning unit, in the alternative case, open-loop controls the tuning of the phase difference using the phase shifter.

An embodiment of the apparatus of the invention provides, that the phase tuning unit, in the case, in which the phase tuning unit closed-loop controls the tuning of the phase difference, compares the parameters required for the closed-loop control with the data stored for the open-loop control, and, in the case of a deviation over a predetermined limit value, updates the data for the open-loop control. The first data for an open-loop control are, for example, acquired and suitably stored in manufacture. Through aging processes or through effects of temperature, pressure, etc. on the measuring device, changes can occur, so that the open-loop control data are no longer suitable. To care for this, in this embodiment, an adaptive learning is performed, in which, in the cases, in which a closed-loop control is possible, the resulting manipulated variable values are compared with the stored control data and, in the case of a deviation over a limit value, the control data are updated. In an additional embodiment, the comparison between the stored data and the current data is used for predictive maintenance.

An embodiment of the apparatus of the invention includes that at least one criterion for judging the measuring of the phase difference is that the two signals have the same frequency and/or the same signal pause ratio and/or the same signal form.

BRIEF DESCRIPTION OF THE DRAWINGS

The invention will now be explained in greater detail on the basis of the appended drawing, the figures of which show as follows.

DETAILED DISCUSSION IN CONJUNCTION WITH THE DRAWINGS

Figure 1:
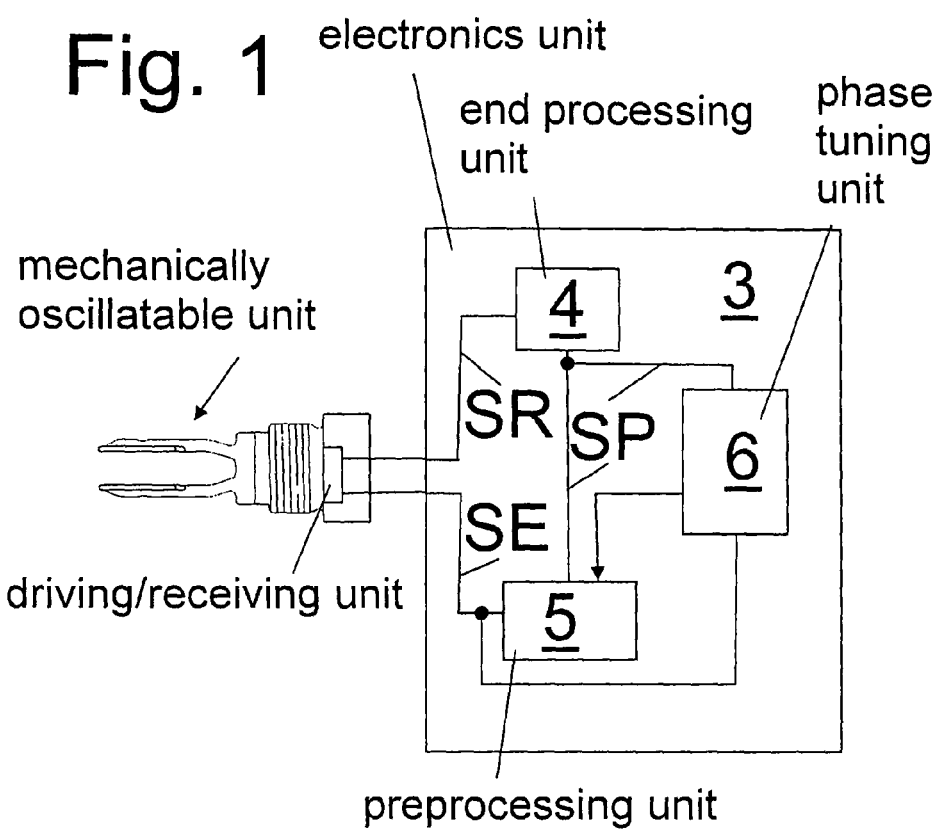
FIG. 1 is a schematic drawing of a measuring device.

FIG. 1 shows, schematically, a measuring device of the invention. The method of the invention is performed with the measuring device of the invention. Shown is a so-called oscillatory fork, which serves as mechanically oscillatable unit 1. The oscillatory fork 1 is excited by a driving/receiving unit 2 to execute mechanical oscillations and/or mechanical oscillations are received by the driving/receiving unit 2 and preferably converted suitably into an electrical signal. For example, the driving/receiving unit 2 is a so-called piezoelectric element, through which changes between mechanical oscillation and electrical alternating voltage take place. The driving/receiving unit 2 is connected with an electronics unit 3, which cares for feedback. Furthermore, the electronics unit 3 receives from the driving/receiving unit 2 the received signal SR and evaluates this in reference to the process variable to be determined and/or monitored, or processes the received signal suitably further. The process variable is, for example, fill level, density, viscosity, flow amount or velocity of the medium. The medium is a liquid or a bulk good or, generally, a fluid. The medium and the container, in which the medium is preferably located, are not shown. In an additional embodiment, the medium is located in a tube, which, in an additional embodiment, is itself the mechanically oscillatable unit.

The electronics unit 3 is here reduced to the components essential for the description of the invention. The electronics unit 3 includes, first, a preprocessing unit 4, to which the received signal SR goes. The preprocessing unit 4 preferably filters the received signal SR and subjects it to a first amplification. From this, there results, then, the preamplified signal SP. This signal SP goes to the end processing unit 5, which produces the actual output, exciter signal SE. The end processing unit 5, among other things, increases the signal to the final amplification. Especially, here, however, it is also to be heeded, that the exciter signal SE must have, relative to the received signal SR, a particular phase difference. This phase difference is important, for example, in order that dependencies of the oscillations on certain process variables can be prevented. Thus, it is, for example, necessary, for the determining and/or monitoring of density, that the dependence of the oscillations, or the oscillation frequency, on viscosity, or on viscosity change, be suppressed.

In order to tune exactly this suitably predetermined phase difference, the phase tuning unit 6 is provided. To the phase tuning unit 6 are sent the preamplified signal SP and the output signal SE. The phase tuning unit 6 ascertains, then, from these two signals the phase difference and closed-loop controls, or open-loop controls, via accessing of the end processing unit 5, this phase difference, until the desired, or predetermined, phase value is reached. In order to change the phase, for example, a phase shifter is provided in the end processing unit 5.

For judging the quality of the determining of the phase difference, according to the invention, at least one criterion is established, which involves, for example, detection of whether the preamplified signal SP and the output signal SE have the same frequency, whether they have the same curve form, or whether the signal pause ratio for both is the same. A further criterion is, for example, also, whether the phase difference resulting from the rising, or falling, edges, is, in each case, the same. Essential is here, however, only, that criteria be established, which can yield a statement as to whether the phase determination is sufficiently reliable that a closed-loop control of the phase difference can be effective.

If these criteria are fulfilled, or, when subcriteria are combined as one criterion, if the criterion is fulfilled, then closed-loop control of the phase difference is performed, in that, for example, the phase tuning unit 6 suitably acts on the end processing unit 5 and the changes at the end processing unit 5 are performed, until the phase difference is the same as the predetermined phase value. Closed-loop control describes here the case, in which a manipulated variable—this is correspondingly given in the end processing unit 5—is altered, until the variable, whose control is desired—this is here the phase difference—equals a desired value, or until the difference between the actual value and the desired value is essentially equal to zero.

If at least one subcriterion, or if the criterion, is not fulfilled, then tuning of the phase difference is performed via open-loop control. For open-loop control, for example, a frequency phase curve of the end processing unit 5 is suitably furnished in the phase tuning unit 6. This means that, from the frequency of the exciter signal SE it can be deduced, which changes are to be effected at the end processing unit 5, so that, in the case of the given frequency, the desired phase is achieved. The frequency can be the frequency of the received signal SR, that of the preamplified signal SP and/or that of the exciter signal SE. Since the exciter signal SE, in most cases, has the greatest amplitude, preferably the frequency of this signal is used.

Another embodiment concerns the fact that the data for the open-loop control of the phase difference should be, as much as possible, optimal. A first set of data, or information, for the open-loop control is preferably taken in the manufacture of the measuring device. In an embodiment, the microcontroller of the measuring device measures the total control loop, in that it passes through a known frequency band and measures, or ascertains, the required control parameters of the closed control loop. This can possibly also happen during normal operations. On occasion required therefor are sufficient computing power, or time, and two switchable, oscillatory circuits. The sensor is adapted to one oscillatory circuit, and the other oscillatory circuit is measured. Then, the procedure is carried out the other way around. Redundant oscillatory circuits make sense, when safety is a concern.

Through aging effects, or, for example, through the effect of the medium on the mechanically oscillatable unit 1, or through process variables, such as temperature and its effect on the electronics unit 3, changes of the individual components can arise. In order to take these aging phenomena into consideration in the case of open-loop control, the control data are preferably updated in the case of the application of the field device, i.e. in the case of the measuring device already installed in the process. For this, in the cases, in which closed-loop control is possible, i.e. when the suitable criteria for judging the quality of the phase difference are fulfilled, the closed-loop control data are suitably compared with the relevant open-loop control data, and, in the case of, deviations outside of a predeterminable limit value, the open-loop control data are adapted to the given closed-loop control data. For applying the open-loop control data, then, on occasion, compensating curves or approximations are suitably adapted to the new characteristic values.

A comparison of the existing, or stored, data with the updated data is used in an embodiment for predictive maintenance, i.e. from the changes of the open-loop control data, changes of the measuring device are deduced and also predictive considerations are employed as regards possible future behavior of the measuring device.

In an additional embodiment, in time intervals and/or through triggering situations, the data for the open-loop control are automatically read in and generally ascertained. I.e., the complete data set for the open-loop control is automatically produced. This happens, for example, in that a microcontroller outputs a frequency band and, while doing so, logs phase.

The measuring device with the method of the invention is, thus, embodied in such a manner, that, in the cases, in which the individual signals have a good quality, i.e. a determining of the phase difference is reliably possible, tuning of the phase difference is performed through a closed-loop control, and that, in the cases, in which the phase difference cannot exactly, or not safely enough, be ascertained, an open-loop control is performed. Used for the open-loop control are stored data, or information regarding the electronics unit. In an additional step, these open-loop control data are suitably adapted, or updated, in the application of the measuring device. This adaptive learning is used in an additional embodiment for predictive maintenance of the measuring device.

Figure 2:
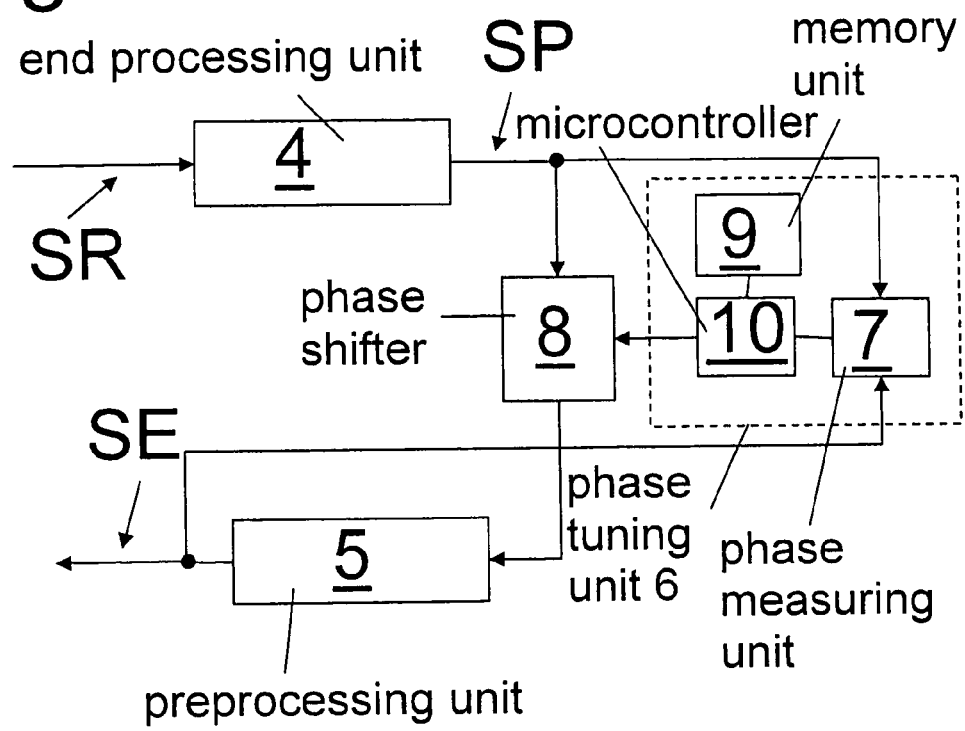
FIG. 2 is a detailed block diagram of the electronics unit of a measuring device.
Figure 3:
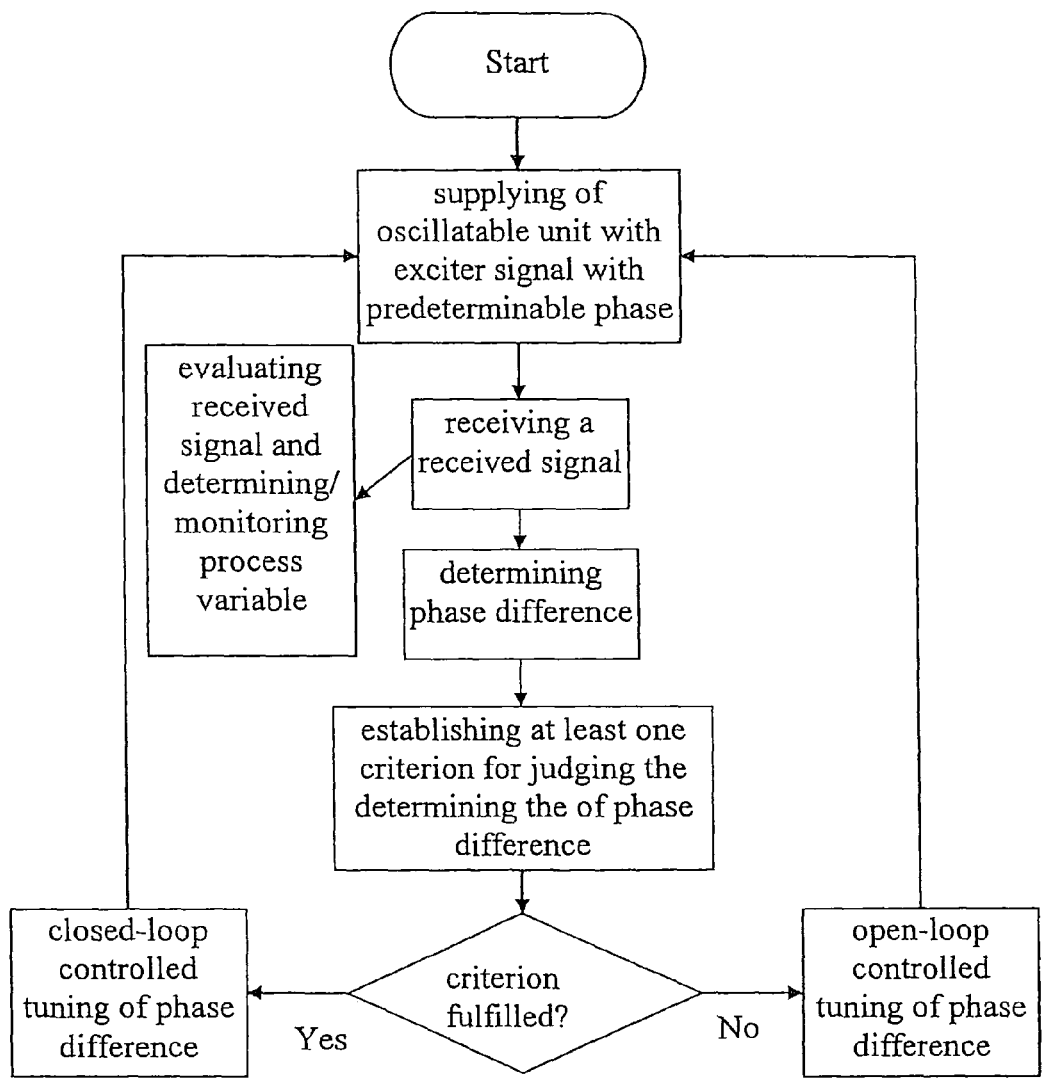
FIG. 3 is a flow diagram illustrating the method for determining and/or monitoring at least one process variable of a medium.

FIG. 2 shows schematically in the form of a block diagram a detailed drawing of the electronics unit 3 of the measuring device. The received signal SR is first filtered and preamplified in a preprocessing unit, which is embodied, for example, in the form of a filter stage. There results, from this, the preamplified signal SP. This preamplified signal SP is here fed to the phase tuning unit 6, in which a phase measuring unit 7 is located. The individual components of the phase tuning unit 6 can be independent units in other embodiments, or, in an additional embodiment, are provided as functions in a microcontroller. This phase measuring unit 7 ascertains, when possible, the phase from the preamplified signal SP. The preamplified signal SP goes, furthermore, to an allpass 8, which here is used as phase shifter. Following passing through the allpass 8 or, after the suitable phase was achieved in the allpass, the so phase-shifted, preamplified signal SP goes to an end processing unit 5, or, for example, especially to an end amplifier, which produces the actual exciter signal SE, which, in turn, goes to the mechanically oscillatable unit, or to its driving/receiving unit, and, thus, produces the further oscillations.

The exciter signal SE is likewise supplied to the phase tuning unit 6, so that also the phase of this signal is ascertained. If the two phase determinations fulfill the stored, quality criteria, then the tuning of difference can be closed-loop controlled on the basis of the ascertained phase difference. In the alternative case, that the criterion is not fulfilled, a closed-loop control is no longer possible and, therefore, tuning of the phase difference is open-loop controlled by means the phase shifter 8. The therefor required control data are stored in a corresponding memory unit 9. For the open-loop control, for example, the frequency of the exciter signal SE is taken into consideration, on the basis of the required frequency phase curve of the allpass being stored in the memory unit.

This means that, in the case of open-loop control, the frequency of the exciter signal SE is measured and then found in a stored table, or in a stored functional dependence, following which the allpass is correspondingly operated as a phase shifter. Thus, in the case, in which the signals, especially the received signal SR or the preamplified signal SP, do not have suitable quality for closed-loop control, it is, nevertheless, possible, to conduct the tuning of the phase very exactly, so that a phase difference required for the measuring can be set.

The data for the open-loop control of the tuning of the phase difference are, for example, suitably stored, via an embodiment, during the manufacture of the measuring device. In an alternative embodiment, these open-loop control data are taken when the measuring device is freshly installed. Disadvantageous with these fixedly stored data is that changes, such as can take place through the application of the device, or through the effects of the medium or the process on the measuring device, are not taken into consideration. Therefore, it is provided in an additional embodiment, that, for the measuring device, or, here, the phase tuning unit 6, in the case, in which a closed-loop control is possible, i.e. in the case, that the occurring signals fulfill the quality criteria, the parameter data resulting from the closed-loop control are compared with the data stored for the open-loop control, and that, in the case of a deviation of the stored data from the current data, the stored data are correspondingly updated. In this embodiment, thus, an adaptive learning is performed, so that the data for the open-loop control are adapted as a function of time and are, thus, optimized. In an additional embodiment, based on the comparison of the current with the stored data, a predictive maintenance is operated.

The invention claimed is:

1. A method for determining and/or monitoring at least one process variable of a medium, wherein:
at least one mechanically oscillatable unit is supplied with an exciter signal, at least one received signal coming from the mechanically oscillatable unit is received and evaluated in reference to at least one process variable to be determined and/or monitored, and the exciter signal is produced such that a phase difference between the exciter signal and said at least one received signal is essentially equal to a predeterminable phase value, the method comprising the steps of:
establishing at least one criterion for judging the determining of the phase difference between the exciter signal and the said at least one received signal, or signals dependent on the exciter signal or on said at least one received signal;
in a case, in which said at least one criterion for judging the determining of the phase difference is fulfilled, tuning of the phase difference is closed-loop controlled; and
in a case, which is alternative to the case where said at least one criterion for judging the determining of the phase difference is fulfilled, tuning of the phase difference is open-loop controlled.

2. The method as claimed in claim 1, wherein:
tuning of the phase difference is closed-loop controlled, until the phase difference is essentially equal to the predeterminable phase value.

3. The method as claimed in claim 1, wherein:
at least one characteristic variable of at least one of the exciter signal and at least one received signal and/or a signal dependent on the exciter signal and/or on at least one received signal is used for open-loop control.

4. The method as claimed in claim 1, further comprising the steps of:
preamplifying at least one received signal to a preamplified signal; and
ascertaining the phase difference between the exciter signal and the preamplified signal and closed-loop controlled or open-loop controlled.

5. The method as claimed in claim 1, wherein:
the frequency of at least one of the exciter signal and/or at least one received signal and the preamplified signal is used for open-loop control of the tuning of the phase difference.

6. The method as claimed in claim 1, wherein:
data produced and stored during manufacture and/or data updated thereafter are used for open-loop control of the tuning of the phase difference.

7. The method as claimed in claim 6, further comprising the step of:
in the case, in which at least one criterion for judging the determining of the phase difference is fulfilled, data for the closed-loop control are compared with data stored and/or updated for the open-loop control of the tuning of the phase difference and in case of a deviation outside of a predetermined limit value, the data for the open-loop control are updated by newly acquired data and are stored.

8. The method as claimed in claim 7, wherein:
the newly acquired data and the stored data are exploited for predictive maintenance.

9. The method as claimed in claim 6, wherein:
in predetermined time intervals, data for open-loop control of tuning of the phase difference are produced automatically.

10. The method as claimed in claim 1, wherein:
an oscillatory fork or a single rod or a membrane, as mechanically oscillatable unit, is supplied with the exciter signal.

11. The method as claimed in claim 1, wherein:
a tube, in which the medium is located at least at times, as the mechanically oscillatable unit, is supplied with the exciter signal.

12. The method as claimed in claim 1, wherein:
at least density or fill level or viscosity or flow of the medium is ascertained and/or monitored.

13. An apparatus for determining and/or monitoring at least one process variable of a medium, comprising:
at least one mechanically oscillatable unit;
at least one driving/receiving unit, which excites said at least one mechanically oscillatable unit to execute mechanical oscillations and which receives mechanical oscillations of said at least one mechanically oscillatable unit;
at least one electronics unit, which supplies said at least one driving/receiving unit with an electrical, exciter signal and which receives from said at least one driving/receiving unit an electrical, received signal; and which evaluated the received signal in reference to the process variable to be determined and/or monitored;
at least one phase measuring unit provided in said at least one electronics unit;
at least one adjustable phase shifter is provided in said at least one electronics unit; and
at least one phase tuning unit is provided in said at least one electronics unit, wherein:
said at least one phase tuning unit judges quality of at least one measuring undertaken by said at least one phase measuring unit of a phase of an electrical signal or a phase difference between two signals; and
said at least one phase tuning unit, based on the judging of the tuning of a phase difference between the exciter signal, or a signal dependent on the exciter signal, and the received signal, or a signal dependent on the received signal, either closed-loop controls or open-loop controls, using said at least one adjustable phase shifter.

14. The apparatus as claimed in claim 13, wherein:
said at least one phase tuning unit, on the basis of at least one predeterminable criterion, judges quality of at least one measuring undertaken by said at least one phase measuring unit of a phase of an electrical signal or a phase difference between two signals.

15. The apparatus as claimed in claim 13, further comprising:
at least one memory unit, in which data for the open-loop control of the tuning of the phase difference are storable.

16. The apparatus as claimed in claim 14, wherein:
said at least one phase tuning unit is embodied in such a manner, that said at least one phase tuning unit, in the case, in which the measuring of the phase or the phase difference fulfills at least one predeterminable criterion, closed-loop controls tuning of the phase difference, using said at least one adjustable phase shifter, and that said at least one phase tuning unit, in the alternative case, open-loop controls tuning of the phase difference, using said at least one adjustable phase shifter.

17. The apparatus as claimed in claim 16, wherein:
said at least one phase tuning unit, in the case, in which said at least one phase tuning unit closed-loop controls tuning of the phase difference, compares with data stored for the open-loop control, parameters required for the closed-loop control, and, in the case of a deviation over a predetermined limit value, updates the data for the open-loop control.

18. The apparatus as claimed in claim 16, wherein:
at least one criterion for judging measuring of the phase difference is that the two signals have at least one of the same frequency and the same signal pause ratio and/or the same signal form.

* * * * *